United States Patent [19]
Ladd et al.

[11] Patent Number: 5,196,580
[45] Date of Patent: Mar. 23, 1993

[54] RECOVERY OF OXALATE FROM SOLUTIONS CONTAINING COMPLEXES OF IRON AND CHROMIUM

[75] Inventors: Judith A. Ladd, Sayre; Michael J. Miller, Towanda, both of Pa.

[73] Assignee: GTE Products Corporation, Danvers, Mass.

[21] Appl. No.: 259,494

[22] Filed: Oct. 17, 1988

Related U.S. Application Data

[63] Continuation of Ser. No. 861,903, May 12, 1986, abandoned.

[51] Int. Cl.$^5$ .................... C07C 51/42; C07C 55/06
[52] U.S. Cl. ..................... 562/593; 562/597
[58] Field of Search ................. 562/593, 597

[56] References Cited

U.S. PATENT DOCUMENTS 3,840,469 10/1974 Hobbs, Jr. et al. ............. 562/597
3,998,878 12/1976 Hearon et al. ............. 562/597
4,303,624 12/1981 Dotson et al. ............. 562/597

FOREIGN PATENT DOCUMENTS 3902 of 1908 United Kingdom ............. 562/597

*Primary Examiner*—José G. Dees
*Assistant Examiner*—Joseph M. Conrad
*Attorney, Agent, or Firm*—Robert E. Walter

[57] ABSTRACT

A method is disclosed for recovering oxalate from oxalate containing solutions containing complexes of iron and chromium. The method involves adjusting the pH of the solution to from about 1 to 2, adding calcium chloride in an amount equal to at least about 3 moles per mole of iron, and digesting the resulting calcium chloride treated solution at at least about 50° C. for a sufficient time to form a solid consisting esssentially of calcium oxalate, followed by separating the solid from the resulting mother liquor.

1 Claim, No Drawings

RECOVERY OF OXALATE FROM SOLUTIONS CONTAINING COMPLEXES OF IRON AND CHROMIUM

This application is a continuation of application Ser. No. 861,903, filed May 12, 1986 abandoned.

BACKGROUND OF THE INVENTION

This invention relates to a method for recovering oxalate from solutions containing complexes of iron and chromium, especially solutions resulting from cobalt processing.

In the processing of material to recover cobalt, solutions are generated which contain oxalates and soluble complexes of iron and chromium.

Cobalt is a strategic metal with many important and industrial applications. Because most of the cobalt used in the United States must be imported, the recovery and recycling of cobalt from scrap and other secondary sources is of considerable interest. Cobalt based superalloys typically contain about 40% to 60% cobalt and about 20% chromium. Following digestion of the superalloy in acid, pH adjustment precipitates the chromium and iron values as chromic and ferric hydroxides. Unfortunately, as much as 5% to 30% of the cobalt can be entrained in the gelatinous precipitate. In the processing of material such as this to recover the cobalt, waste solutions are generated which contain oxalate and soluble complexes of iron and chromium. It would be desirable from an economic standpoint to recover the oxalate.

U.S. Pat. No. 4,184,868 relates to a method for producing extra fine cobalt metal powder by digesting cobalt pentammine choride in ammonium hydroxide to obtain a black precipitate which contains cobalt and which is thereafter reduced to metal powder. U.S. Pat. Nos. 4,214,894, 4,233,063, and 4,278,463 relate to improvements in 4,184,868 in which the ammonia solutions are processed to recover any cobalt therein. U.S. Pat. Nos. 4,395,278 and 4,469,505 relate to improvements in 4,184,868 in which fine cobalt metal powder is produced having reduced tailings.

U.S. Pat. No. 4,214,895 relates to a process for producing cobalt metal powder which involves treating an aqueous solution of a soluble cobaltic ammine halide with a sufficient amount of a soluble metallic hydroxide to form a cobalt containing precipitate which is thereafter reduced to metallic cobalt.

U.S. Pat. No. 4,218,240 relates to a method for producing cobalt metal powder by forming a solution of a cobalt hexammine compound and treating the solution with a metallic hydroxide to form a precipitate which is reduced to cobalt metal powder. U.S. Pat. Nos. 4,348,224 and 4,381,937 relate to improvements in the process described in U.S. Pat. No. 4,218,240 which involve removal of copper and silver from the cobalt. U.S. Pat. No. 4,452,633 relates to an improvement in the processes described in U.S. Pat. Nos. 4,218,240 and 4,348,224 in which the silver is recovered.

U.S. Pat. No. 4,093,450 to Doyle et al describes a process for producing fine particle size cobalt metal powder by the hydrogen reduction of cobalt oxide obtained from a cobalt pentammine carbonate solution. The precipitate is formed by heating the solution to drive off ammonia and carbon dioxide to form a precipitate od cobalt oxide. This process requires a solution of about 4 grams of cobalt per liter to produce a metal powder having a particle size of less than about 1 micron. Note that the final resulting particle size of less than about 1 micron is highly dependent on the concentration of cobalt employed in the aqueous solution.

U.S. Pat. No. 4,329,169 relates to a process for producing fine cobalt metal powder absent tailings by heating an aqueous solution of soluble cobalt ammine halide to decompose the halide and form a cobalt containing precipitate which is reduced to the cobalt metal powder.

U.S. Pat. No. 4,409,019 relates to a process for producing fine cobalt metal powder from pieces of relatively pure cobalt by dissolving the cobalt pieces in an aqueous solution of hydrogen iodide and iodine and forming a cobalt containing solid which is subsequently reduced to a fine cobalt metal powder.

SUMMARY OF THE INVENTION

In accordance with one aspect of this invention, there is provided a method for recovering oxalate from oxalate containing solutions containing complexes of iron and chromium. The method involves adjusting the pH of the solution to from about 1 to 2, adding calcium chloride in an amount equal to at least about 3 moles per mole of iron, and digesting the resulting calcium chloride treated solution at at least about 50° C. for a sufficient time to form a solid consisting essentially of calcium oxalate, followed by separating the solid from the resulting mother liquor.

DETAILED DESCRIPTION OF THE INVENTION

For a better understanding of the present invention, together with other and further objects, advantages and capabilities thereof, reference is made to the following disclosure and appended claims in connection with the above description of some of the aspects of the invention.

The starting solutions of this invention contain oxalate and soluble complexes of iron and chromium. The oxalate is present typically at at least about 3 moles per mole of iron because the iron is present typically as the tris-oxalato iron complex. The preferred source of the starting solution is the waste solutions produced from processing to recover cobalt. In cobalt processing, materials are generated which contain too much cobalt to be discarded. They are therefore processed to recover the cobalt. This can be done by precipitating cobalt as the oxalate. This results in liquors containing large amounts of oxalate. These solutions contain iron $+3$ and chromium $+3$ complexes, typically as the tris-oxalate complex and a hydrated chromium complex respectively.

The pH of the starting solution is adjusted to from about 1.0 to about 2.0 with an acid which is preferably hydrochloric acid. Use of sulfuric acid results in subsequent formation of insoluble calcium sulfate thereby wasting the calcium. Therefore it is preferred not to use sulfuric acid.

Calcium chloride is then added to the resulting pH adjusted solution. Since the oxalate is complexed with the iron as a tris-oxalato complex in which 3 moles of oxalate are present per mole of iron, the amount of calcium chloride that is needed is equal to at least about 3 moles per mole of iron. It is desirable to add calcium chloride in excess of this amount.

The resulting calcium chloride treated solution is then digested preferably with agitation at a temperature of at least about 50° C., and preferably at about 75° C. to about 100° C. for a sufficient time, preferably at least about 2 hours to form a solid consisting essentially of calcium oxalate. In actual practice it is preferred to first heat the pH adjusted solution to at least about 80° C. prior to the addition of the calcium chloride. At least about 90% by weight of the oxalate which was present in the starting solution is recovered in the solid. The solid is then separated from the resulting mother liquor by any standard technique such as filtration.

It is preferred to wash the calcium oxalate solid with dilute HCl preferably at a pH of about 1.5 to remove soluble impurities.

The calcium oxalate solid is then dried at a temperature of about room temperature or greater.

The calcium oxalate so recovered can be converted to a form usable as the oxalate source in this invention, such as oxalic acid dihydrate and reused.

To more fully illustrate this invention, the following non-limiting example is presented. All parts, portions, and percentages are on a weight basis unless otherwise stated. Example About 500 ml of the liquor resulting from the precipitation of cobalt oxalate containing <0.05 g Co/l, about 12 g Fe/l, about 7.4 g Cr/l, and about 0.025 g Ni/l are heated in a 2 l beaker with stirring. Since the initial pH of the solution is <3.0, HCl is added to adjust the pH to about 1.5. Excess solid calcium chloride, about 50 g is added and the reaction mixture is heated at about 80° C. for an additional 2 hours. The heat source is removed and the reaction mixture is cooled and filtered. After washing the precipitate with dilute HCl, the combined volume of the filtrate and washings totals about 610 ml. The precipitate weighs about 43.41 g after drying at about 110° C. The precipitate is analyzed by x-ray diffraction analysis and is identified as $CaC_2O_4 \cdot H_2O$.

Based on the reaction stoichiometry for the cobalt oxalate precipitation process which requires 3 moles of oxalate per mole of iron but none for chromium, the theoretical yield of $CaC_2O_4 \cdot H_2O$ under these conditions is about 46.98 g. Thus, the observed weight of precipitate (43.41 g) corresponds to a yield of about 92% on the recovery of oxalate.

While there has been shown and described what are at present considered the preferred embodiments of the invention, it will be obvious to those skilled in the art that various changes and modifications may be made therein without departing from the scope of the invention as defined by the appended claims.

What is claimed is:

1. A method for recovering oxalate from oxalate containing solutions containing complexes of iron and chromium as tris-oxalato iron complex and hydrated chromium complex, respectively, said method consisting essentially of:
   a) adjusting the pH of said oxalate containing solution to from about 1 to about 2 with hydrochloric acid;
   b) heating the resulting pH adjusted solution to at least about 80° C.;
   c) adding calcium chloride to said pH adjusted solution in an amount equal to at least about 3 moles per mole of iron;
   d) digesting the resulting calcium chloride treated solution at a temperature of at least about 50° C. for a sufficient time to form a solid consisting essentially of calcium oxalate wherein said solid contains at least about 90% by weight of the oxalate in said oxalate containing solution; and
   e) separating said solid from the resulting mother liquor.

* * * * *